(12) United States Patent
Wolf

(10) Patent No.: US 8,465,560 B1
(45) Date of Patent: Jun. 18, 2013

(54) GASOLINE DEPOSIT CONTROL ADDITIVE COMPOSITION

(75) Inventor: Leslie R. Wolf, Naperville, IL (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 272 days.

(21) Appl. No.: 12/697,590

(22) Filed: Feb. 1, 2010

Related U.S. Application Data

(60) Provisional application No. 61/150,045, filed on Feb. 5, 2009.

(51) Int. Cl.
*C10L 1/22* (2006.01)

(52) U.S. Cl.
USPC .................................. 44/421; 44/420; 44/340

(58) Field of Classification Search
USPC .................... 44/340, 412, 420, 421, 434, 451, 44/452
See application file for complete search history.

(56) References Cited

U.S. PATENT DOCUMENTS

| | | | |
|---|---|---|---|
| 2,622,018 A | 12/1952 | White et al. | |
| 3,438,757 A | 4/1969 | Honnen et al. | |
| 3,565,804 A | 2/1971 | Honnen et al. | |
| 3,574,576 A | 4/1971 | Honnen et al. | |
| 3,848,056 A | 11/1974 | Fonseca | |
| 3,849,083 A | 11/1974 | Dubeck | |
| 3,960,515 A | 6/1976 | Honnen et al. | |
| 4,160,648 A | 7/1979 | Lewis et al. | |
| 4,191,537 A | 3/1980 | Lewis et al. | |
| 4,197,409 A | 4/1980 | Lilburn | |
| 4,233,168 A | 11/1980 | Lewis et al. | |
| 4,236,020 A | 11/1980 | Lewis et al. | |
| 4,243,798 A | 1/1981 | Franklin et al. | |
| 4,270,930 A | 6/1981 | Campbell et al. | |
| 4,288,612 A | 9/1981 | Lewis et al. | |
| 4,292,046 A | 9/1981 | Piotrowski | |
| 4,347,109 A * | 8/1982 | Meshbesher | 568/853 |
| 4,398,921 A | 8/1983 | Rifkin et al. | |
| 4,409,000 A | 10/1983 | LeSuer | |
| 4,518,782 A | 5/1985 | Sung et al. | |
| 4,729,769 A | 3/1988 | Schlicht et al. | |
| 4,810,263 A | 3/1989 | Zimmerman et al. | |
| 4,832,702 A | 5/1989 | Kummer et al. | |
| 4,836,829 A | 6/1989 | Zimmerman et al. | |
| 4,881,945 A | 11/1989 | Buckley, III | |
| 4,978,366 A | 12/1990 | Weers | |
| 5,006,130 A | 4/1991 | Aiello et al. | |
| 5,112,364 A | 5/1992 | Rath et al. | |
| 5,139,534 A | 8/1992 | Tomassen et al. | |
| 5,197,997 A * | 3/1993 | Mozdzen et al. | 44/386 |
| 5,393,309 A | 2/1995 | Cherpeck | |
| 5,567,212 A * | 10/1996 | Gentry et al. | 44/420 |
| 5,588,973 A | 12/1996 | Blackborow et al. | |
| 5,618,320 A | 4/1997 | Cherpeck | |
| 5,620,486 A | 4/1997 | Cherpeck | |
| 5,669,939 A | 9/1997 | Cherpeck | |
| 5,749,929 A | 5/1998 | Cherpeck et al. | |
| 5,830,243 A * | 11/1998 | Wolak et al. | 44/336 |
| 5,851,242 A | 12/1998 | Cherpeck et al. | |
| 5,916,825 A | 6/1999 | Cherpeck | |
| 5,954,843 A | 9/1999 | Cherpeck | |
| 5,993,497 A | 11/1999 | Cherpeck et al. | |
| 6,114,542 A | 9/2000 | Cherpeck | |
| 6,117,197 A * | 9/2000 | Houser | 44/389 |
| 6,203,584 B1 | 3/2001 | Fuentes-Afflick et al. | |
| 6,217,624 B1 | 4/2001 | Morris et al. | |
| 6,652,667 B2 | 11/2003 | Ahmadi et al. | |
| 6,660,050 B1 * | 12/2003 | Dieckmann et al. | 44/412 |
| 2004/0123516 A1 * | 7/2004 | Hull et al. | 44/349 |
| 2007/0094922 A1 | 5/2007 | Bergemann et al. | |
| 2007/0178567 A1 * | 8/2007 | Lewis | 435/161 |
| 2008/0066377 A1 | 3/2008 | Cunningham | |

FOREIGN PATENT DOCUMENTS

| | | |
|---|---|---|
| EP | 149486 | 1/1985 |
| EP | 0902079 | 3/1999 |
| EP | 0950704 | 10/1999 |
| EP | 1122295 | 8/2001 |
| EP | 1132454 | 9/2001 |
| GB | 985373 | 3/1965 |
| GB | 1083712 | 9/1967 |
| GB | 1486144 | 3/1975 |
| WO | 9010051 | 9/1990 |
| WO | 9511286 | 4/1995 |
| WO | 9730103 | 8/1997 |
| WO | 2007039488 | 4/2007 |

OTHER PUBLICATIONS

Jeffamine M-600 (evidentiary reference).*
Jeffamine M-600.*
STIC Search 12 2011.*
International Search Report and Written Opinion of corresponding PCT/US2010/023027 mailed Jun. 15, 2010.

* cited by examiner

*Primary Examiner* — Pamela H Weiss
(74) *Attorney, Agent, or Firm* — Christine M. Lhulier

(57) ABSTRACT

A gasoline deposit control additive composition for use in a fuel comprising from about 70 to about 95 volume percent of hydrocarbons in the gasoline boiling range and from about 5 to about 30 volume percent of at least one alcohol, comprising the imine or tertiary amine product of the reaction between (a) at least one aldehyde or ketone or mixture thereof having the formula $R_{16}$CHO, $R_{16}$CH$_2$CHO, $R_{17}$(C=O)$R_{18}$ or $R_{17}$CH$_2$(C=O)$R_{18}$, wherein $R_{16}$, $R_{17}$, and $R_{18}$ are the same or different and are each independently a straight or branched chain hydrocarbyl or aryl group that contains from 1 to 18 carbon atoms, and (b) a primary or secondary amine functionality.

11 Claims, No Drawings

GASOLINE DEPOSIT CONTROL ADDITIVE COMPOSITION

CROSS REFERENCE TO RELATED APPLICATIONS

This application is related to and claims the benefit of priority to U.S. Provisional Application No. 61/150,045 filed Feb. 5, 2009, the entirety of which is herein incorporated by reference.

FIELD OF THE INVENTION

The invention relates to the field of detergent additive compositions, particularly to gasoline deposit control additive compositions, for use in gasoline containing an alcohol component.

BACKGROUND OF THE INVENTION

Detergent additives are required in fuels in order to control intake-valve deposits that can cause increased emissions from vehicles. Generally these additives have amine functionality, typically primary or secondary amines or both, and a hydrocarbyl chain that is compatible with the fuel. The amine functionality binds to the intake-valve deposits, and the chain allows solubilization either in the liquid fuel or a carrier fluid that may be included in the detergent control additive package. The amine's base strength and the chain's composition are carefully chosen to provide optimum performance. The importance of controlling intake-valve deposits so that emissions are not increased has led the United States Environmental Protection Agency (EPA) to mandate the use of detergent additives (also known as deposit control additives or DCA's) in all on-road gasoline for use in the United States.

Worldwide concern over the growing shortages of crude oil supplies has promoted the use of many materials as blending agents in gasoline to extend the fuel supply. From the engine or motor vehicle manufacturers' point of view, it seems easiest to employ alcohol blended with gasoline. Methanol, ethanol and butanol have emerged as the most widely used alcohol blending agents. A high level of interest has been shown in the use of "gasohol," defined herein as a blend of gasoline with from about 5 to about 30 volume percent ethanol, as an automotive fuel. Interest has been especially high in countries such as Brazil which have an intense cultivation of sugar cane, mandioca and other raw materials of vegetable origin adequate for the production of ethanol.

The use of a polar oxygenate such as an alcohol in gasoline blends, however, has far reaching consequences. One of these is the formation of deposits in the fuel induction system such as the carburetor or fuel injector and around the intake valves. These deposits interfere with the efficient operation of the engine and can lead to lower mileage and increased exhaust emissions. It is believed that deposit formation may be caused by several factors. One of these may be the loosening of rust by the alcohol from the walls in pipelines and storage tanks which is then transported through the system until it finds its way into the fuel induction system of the engine.

Another factor may be the presence of trace amounts of acetic acid, acetaldehyde, ethyl acetate and n-butanol in alcohol-gasoline blends which are formed during the production of the alcohol during fermentation. Biofuels such as ethanol and butanols that are made by fermentation processes often contain carbonyl compounds, in particular, aldehydes and ketones, which can react with conventional nitrogen-containing deposit control additives, to form imines or more highly substituted amines by various addition or condensation reactions. For example, fermentation processes can produce acetone, which during purification of the desired alcohol product can form diacetone alcohol, a hydroxyl ketone and its dehydration product, mesityl oxide, an unsaturated ketone. Other ketones and aldehydes can produce corresponding condensation products. These impurities likewise may ultimately end up in the fuel induction system of the engine and contribute to deposit formation. Also the aldehydes and ketones could react with the amine functionality of the detergent additive and reduce its effectiveness. Often the amount of carbonyl compounds present is more than that which would be stoichiometrically required to react with all the amine functionality.

Other factors which may contribute to deposit formation are phase separation which may occur because commercial alcohol has limited solubility in gasoline and the presence of dissolved mineral salts, such as sodium sulfate, which may find their way into the fuel during production, storage and transportation.

Furthermore, alcohol-gasoline blends have different solvency characteristics than non-oxygenated gasoline. This change in solvency can impede the detergent additive performance because the carefully chosen amine base strength and chain composition described previously behaves differently in this medium. In extreme cases of altered compatibility between the detergent additive and the alcohol gasoline blend, the detergent additive can precipitate from solution or insolubilize on the engine's intake valves causing sticking during start-up at cold temperatures.

For enhanced intake-valve keep-clean and clean-up performance recent fuel trends have been to use higher concentrations than the minimum required by the EPA for a particular detergent additive. For example, each detergent additive or deposit control additive, DCA is assigned a "lowest additive concentration" or LAC by the EPA based on its ability to prevent intake-valve deposits as measured by a prescribed test. To meet EPA regulations a one times (1x) treat rate at this concentration level is required. Auto manufacturers, such as General Motors in its Top Tier Program, have recommended the use of higher levels, for example, 2x (or two times) LAC, to provide improved performance of their engines. At high concentrations, low-temperature valve-sticking becomes a critical issue because the high concentration can leave a film of sticky additive on the intake-valve stem causing the valve to remain open during cold-starting. The formation of the sticky film depends on the compatibility of the additive formulation. Good compatibility of an additive formulation corresponds to the formulation being very soluble in fuel (that is, gasoline or alcohol-gasoline blend). However, the change in solvency of alcohol-gasoline blends can upset this compatibility. The concentration and type of the alcohols as well as the additive's composition influence this compatibility. Furthermore, some additive formulations contain a high boiling fluidizer that is very compatible with the additive and that acts to wash the sticky additive off the intake-valve stem.

Thus, there is presently a need for a fuel induction detergent that will either retard or prevent the formation of deposits in the fuel induction system of an internal combustion engine operated on an alcohol-gasoline fuel mixture. Further, it is important that the detergent be effective in very small quantities in order to minimize cost and to avoid adverse effects, such as adding to the gum component of the fuel, increasing combustion chamber deposits, etc. Also it is desirable for the detergent to be immune to the presence of carbonyl compounds and not to cause valve-sticking during start-up at low temperature.

Several detergent compositions have been disclosed. For example, U. S. Pat. No. 4,398,921 discloses a fuel for internal combustion engines comprising from about 70 to about 90 volume percent of hydrocarbons boiling in the gasoline boiling range, from about 5 to about 30 volume percent of ethanol and a detergent amount of a mixture of (1) a mononuclear or dinuclear aromatic hydrocarbon solvent, (2) a hydrocarbyl succinic acid or anhydride corrosion inhibitor (3) a demulsifying agent containing at least one oil-soluble polyether and an oxyalkylated phenol formaldehyde resin, and (4) a Mannich product formed by the reaction between an alkylphenol, an aldehyde and an amine having at least one active hydrogen atom bonded to an amino nitrogen atom.

U. S. Pat. No. 6,652,667 discloses a method for removing engine deposits in a gasoline internal combustion engine by introducing a cleaning composition into a air-intake manifold of a warmed-up and idling gasoline internal combustion engine and running the engine while the cleaning composition is being introduced. The cleaning composition comprises (1) a phenoxy mono- or poly(oxyalkylene) alcohol, (2) at least one solvent selected from an alkoxy mono- or poly (oxyalkylene) alcohol and an aliphalic or aromatic solvent, and (3) at least one nitrogen-containing detergent additive. Useful nitrogen-containing detergent additives include all of the nitrogen-containing compounds that are suitable for use in the formation of the nitrogen-containing detergent compositions of the present invention.

PCT patent application number PCT/EP2006/066623, published as WO 2007/039488 A1, discloses hydroxyalkyl-substituted amino-alkylamides of fatty acids for use as friction modifying agents for fuels such as gasolines containing oxygenated compounds such as ethanol. These amides are formed by reacting a specific class of amines with a carboxylic acid or a carboxylic acid derivative thereof which is capable of reacting with an amine to form an amide. If the resulting amide product contains an active hydrogen atom bonded to an amino nitrogen atom, the amide product is further reacted with an alkylene oxide.

US2007/0094922 A1 discloses compositions which comprise at least one polyalkene amine in a solvent for improving the intake system-cleaning action of fuels which can contain up to 25 percent by volume of oxygen containing materials such as alcohols and ethers. The polyalkene amines employed are those whose polyalkene moiety is the polymerization product of identical or different, straight chain or branched $C_2$ - $C_6$ olefin monomers.

Published U.S. patent application No. US2008/0066377 A1 discloses a biodegradable fuel detergent additive composition for use in gasoline and diesel fuel, including fuels containing alcohols. The detergent additive can be selected from the group consisting of polyamines, polyetheramines, succinimides, succinamides, aliphatic polyamines and Mannich detergents.

SUMMARY OF THE INVENTION

The present invention is a deposit control additive for use in a liquid automotive fuel comprising from about 70 to about 95 volume percent of hydrocarbons boiling in the gasoline range and from about 5 to about 30 volume percent of at least one alcohol, comprising an imine or tertiary amine product of the reaction between (a) at least one aldehyde or ketone or mixture thereof having the formula $R_{16}$CHO, $R_{16}$CH$_2$CHO, $R_{17}$(C=O)$R_{18}$ or $R_{17}$CH$_2$(C=O)$R_{18}$, wherein $R_{16}$, $R_{17}$ and $R_{18}$ are the same or different and are each independently a straight or branched chain hydrocarbyl or aryl group that contains from 1 to 18 carbon atoms, with (b) a primary or secondary amine functionality in at least one nitrogen-containing compound selected from the group consisting of aliphatic hydrocarbyl amines, hydrocarbyl-substituted poly (oxyalkylene) amines, hydrocarbyl-substituted succinimides, Mannich reaction products, polyalkylphenoxyaminoalkanes, nitro and amino aromatic esters of polyalkylyphenoxyalkanols, a carburetor/injector detergent additive having a molecular weight in the range from 100 to 600 and having a non-polar moiety and nitrogen-containing polar moiety, and mixtures thereof.

DETAILED DESCRIPTION OF THE INVENTION

The deposit control additives employed in the present invention are reaction products of certain aldehydes or ketones with the following conventional unmodified nitrogen-containing detergent additives disclosed in U.S. Pat. No. 6,652,667: aliphatic hydrocarbyl amines, hydrocarbyl-substituted poly(oxyalkylene) amines, hydrocarbyl-substituted succinimides, Mannich reaction products, polyalkylphenoxyaminoalkanes, nitro and amino aromatic esters of polyalkylphenoxyalkanols, carburetor/injector detergent additives having a molecular weight in the range of from 100 to 600 and having a non-polar moiety and nitrogen-containing polar moiety, or mixtures thereof.

The aliphatic hydrocarbyl-substituted amines which may be employed as reactants in the manufacture of the deposit control additives of the present invention are typically straight or branched chain hydrocarbyl-substituted amines having at least one basic nitrogen atom and wherein the hydrocarbyl group has a number average molecular weight of about 400 to 3,000. Preferred aliphatic hydrocarbyl-substituted amines include polyisobutenyl and polyisobutyl monoamines and polyamines. Such aliphatic hydrocarbyl amines can be prepared by conventional procedures known in the art. Suitable preparations are described in detail in U.S. Pat. Nos. 3,438,757; 3,565,804; 3,574,576; 3,848,056; 3,960,515; 4,832,702; and 6,203,584, the disclosures of which are incorporated herein by reference.

The deposit control additives of the present invention are intended for use in automotive fuels containing from about 5, preferably from about 2, to about 30 volume percent, preferably to about 20 volume percent of at least one alcohol. The alcohol can be methanol, ethanol, propyl or butyl alcohol and preferably is a butyl alcohol isomer.

Another class of deposit control additives suitable for use as reactants in the manufacture of the detergent additives of the present invention are the hydrocarbyl-substituted poly (oxyalkylene) amines, also referred to as polyether amines. Typical hydrocarbyl-substituted poly(oxyalkylene) amines include hydrocarbyl poly(oxyalkylene) monoamines and polyamines wherein the hydrocarbyl group contains from 1 to about 30 carbon atoms, the number of oxyalkylene units will range from about 5 to 100, and the amine moiety is derived from ammonia, a primary alkyl or secondary dialkyl monoamine, or a polyamine having a terminal amino nitrogen atom. Preferably, the oxyalkylene moiety will be oxypropylene or oxybutylene or a mixture thereof. Such hydrocarbyl-substituted poly(oxyalkylene) amines are described, for example, in U.S. Pat. Nos. 6,217,624 and 5,112,364, the disclosures of which are incorporated herein by reference.

A preferred type of hydrocarbyl-substituted poly(oxyalkylene) monoamine is an alkylphenyl poly(oxyalkylene)monoamine wherein the poly(oxyalkylene) moiety contains oxypropylene units or oxybutylene units or mixtures of oxypropylene and oxybutylene units. Preferably, the alkyl group on the alkylphenyl moiety is a straight or branched-chain alkyl of 1 to 24 carbon atoms. An especially preferred alkylphenyl moiety is tetrapropenylphenyl, that is, where the alkyl group is a branched-chain alkyl group of 12 carbon atoms derived from propylene tetramer.

An additional type of hydrocarbyl-substituted poly(oxyalkylene)amine for use as reactants in the manufacture of the deposit control additives of the present invention is hydrocarbyl-substituted poly(oxyalkylene) aminocarbamates disclosed, for example, in U.S. Pat. Nos. 4,288,612; 4,236,020; 4,160,648; 4,191,537; 4,270,930; 4,233,168; 4,197,409; 4,243,798 and 4,881,945, the disclosures of which are incorporated herein by reference. These hydrocarbyl poly(oxyalkylene) aminocarbamates contain at least one basic nitrogen atom and have an average molecular weight of about 500 to 10,000, preferably about 500 to 5,000, and more preferably about 1,000 to 3,000. A preferred aminocarbamate is alkylphenyl poly(oxybutylene) aminocarbamate wherein the amine moiety is derived from ethylene diamine or diethylene triamine.

A further class of detergent additives suitable for use as reactants in the manufacture of the deposit control additives of the present invention is the hydrocarbyl-substituted succinimides. Typical hydrocarbyl-substituted succinimides include polyalkyl and polyalkenyl succinimides wherein the polyalkyl or polyalkenyl group has an average molecular weight of about 500 to 5,000, and preferably about 700 to 3,000. The hydrocarbyl-substituted succinimides are typically prepared by reacting a hydrocarbyl-substituted succinic anhydride with an amine or polyamine having at least one reactive hydrogen bonded to an amine nitrogen atom. Preferred hydrocarbyl-substituted succinimides include polyisobutenyl and polyisobutanyl succinimides, and derivatives thereof. The hydrocarbyl-substituted succinimides are described, for example, in U.S. Pat. Nos. 5,393,309; 5,588,973; 5,620,486; 5,916,825; 5,954,843; 5,993,497; and 6,114,542, and British Patent No. 1,486,144, the disclosures of which are incorporated herein by reference.

Yet another class of detergent additives which can be employed as reactants in the manufacture of the deposit control additives of the present invention is Mannich reaction products which are typically obtained from the Mannich condensation of a high molecular weight alkyl-substituted hydroxyaromatic compound, an amine containing at least one reactive hydrogen, and an aldehyde. The high molecular weight alkyl-substituted hydroxyaromatic compounds are preferably polyalkylphenols, such as polypropylphenol and polybutylphenol, especially polyisobutylphenol, wherein the polyakyl group has an average molecular weight of about 600 to 3,000. The amine reactant is typically a polyamine, such as alkylene polyamines, especially ethylene or polyethylene polyamines, for example, ethylene diamine, diethylene triamine, triethylene tetramine, and the like. The aldehyde reactant is generally an aliphatic aldehyde, such as formaldehyde, paraformaldehyde, formalin, and acetaldehyde. A preferred Mannich reaction product is obtained by condensing a polyisobutylphenol with formaldehyde and diethylene triamine, wherein the polyisobutyl group has an average molecular weight of about 1,000. The Mannich reaction products are described, for example, in U.S. Pat. Nos. 4,231,759 and 5,697,988, the disclosures of which are incorporated herein by reference.

A still further class of detergent additives suitable for use as reactants in the manufacture of the deposit control additives of the present invention are polyalkylphenoxyaminoalkanes. Preferred polyalkylphenoxyaminoalkanes include those having the formula:

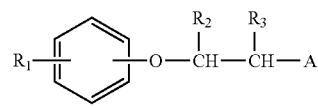

wherein: $R_1$ is a polyalkyl group having an average molecular weight in the range of about 600 to 5,000; $R_2$ and $R_3$ are independently hydrogen or lower alkyl having 1 to 6 carbon atoms; and A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms. The polyalkylphenoxyaminoalkanes of Formula I above and their preparations are described in detail in U.S. Pat. No. 5,669,939, the disclosure of which is incorporated herein by reference. Mixtures of polyalkylphenoxyaminoalkanes and poly(oxyalkylene) amines are also suitable for use as reactants in the manufacture of the detergent additives of the present invention. These mixtures are described in detail in U.S. Pat. No. 5,851,242, the disclosure of which is incorporated herein by reference.

A preferred class of detergent additives finding use as reactants in the manufacture of the deposit control additives of the present invention are nitro and amino aromatic esters of polyalkylphenoxyalkanols. Preferred nitro and amino aromatic esters of polyalkylphenoxyalkanols include those having the formula:

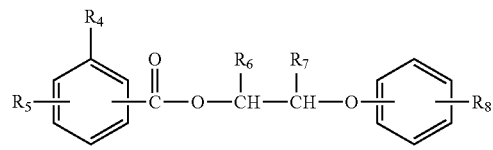

wherein: $R_4$ is nitro or —$(CH_2)_n$—$NR_9 R_{10}$, wherein $R_9$ and $R_{10}$ are independently hydrogen or lower alkyl having 1 to 6 carbon atoms and n is 0 or 1; $R_5$ is hydrogen, hydroxy, nitro or —$NR_{11} R_{12}$, wherein $R_{11}$ and $R_{12}$ are independently hydrogen or lower alkyl having 1 to 6 carbon atoms; $R_6$ and $R_7$, are independently hydrogen or lower alkyl having 1 to 6 carbon atoms; and $R_8$ is a polyalkyl group having an average molecular weight in the range of about 450 to 5,000. The aromatic esters of polyalkylphenoxyalkanols shown in Formula II above and their preparations are described in detail in U.S. Pat. No. 5,618,320, the disclosure of which is incorporated herein by reference.

Mixtures of nitro and amino aromatic esters of polyalkylphenoxyalkanols and hydrocarbyl-substituted poly(oxyalkylene) amines are also preferably contemplated for use as reactants in the manufacture of the deposit control additives of the present invention. These mixtures are described in detail in U.S. Pat. No. 5,749,929, the disclosure of which is incorporated herein by reference. Preferred hydrocarbyl-substituted poly(oxyalkylene) amines which may be employed as detergent additives in the present invention include those having the formula:

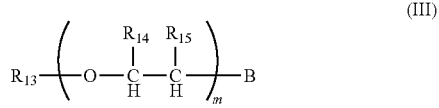

wherein: $R_{13}$ is a hydrocarbyl group having from about 1 to about 30 carbon atoms; $R_{14}$ and $R_{15}$ are each independently hydrogen or lower alkyl having about 1 to about 6 carbon atoms and each $R_{14}$ and $R_{15}$ is independently selected in each —O—$CHR_{14}$—$CHR_{15}$—unit; B is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and m is an integer from about 5 to about 100. The hydrocarbyl-substituted poly(oxyalkylene) amines of Formula III above and their preparations are described in detail in U.S. Pat. No. 6,217,624, the disclosure of which is incorporated herein by reference.

The hydrocarbyl-substituted poly(oxyalkylene) amines of Formula III are preferably utilized either by themselves or in combination with other aforesaid unmodified deposit control additives, particularly with the polyalkylphenoxyaminoalkanes of Formula I or the nitro and amino aromatic esters of polyalkylphenoxyalkanols shown in Formula II, as reactants in the manufacture of the detergent additives of the present invention. More preferably, combinations of the hydrocarbyl-substituted poly(oxyalkylene) amines of Formula III with the nitro and amino aromatic esters of polyalkylphenoxyalkanols shown in Formula II are employed together as reactants in the manufacture of the detergent additives of the present invention. A particularly preferred hydrocarbyl-substituted poly(oxyalkylene) amine is dodecylphenoxy poly(oxybutylene) amine and a particularly preferred combination is the combination of dodecylphenoxy poly(oxybutylene) amine and 4-polyisobutylphenoxyethyl para-aminobenzoate.

Another class of conventional deposit control additives suitable for use as reactants in the manufacture of the deposit control additives of the present invention is the nitrogen-containing carburetor/injector detergents. The carburetor/injector detergent additives are typically relatively low molecular weight compounds having a number average molecular weight of about 100 to about 600 and possessing at least one polar moiety and at least one non-polar moiety. The non-polar moiety is typically a linear or branched-chain alkyl or alkenyl group having about 6 to about 40 carbon atoms. The polar moiety is typically nitrogen-containing Typical nitrogen-containing polar moieties include amines (for example, as described in U.S. Pat. No. 5,139,534 and PCT International Publication Number WO 90/10051), ether amines (for example, as described in U.S. Pat. No. 3,849,083 and PCT International Publication Number WO 90/10051), amides, polyamides and amide-esters (for example, as described in U.S. Pat. Nos. 2,622,018; 4,729,769; and 5,139,534; and European Patent Publication Number 149,486), imidazolines (for example, as described in U.S. Pat. No. 4,518,782), amine oxides (for example, as described in U.S. Pat. Nos. 4,810,263 and 4,836,829), hydroxyamines (for example, as described in U.S. Pat. No. 4,409,000), and succinimides (for example, as described in U.S. Pat. No. 4,292,046).

The compositions of the detergent or deposit control additives of the present invention are the imine or tertiary amine products of the reaction between the aforesaid unmodified conventional deposit control additive compositions described above and selected aldehydes or ketones of low (less than 100) carbon number. Each of the above described unmodified deposit control additives contains a primary and/or secondary amine functionality, which functionality can be modified by reaction with suitable low carbon number aldehydes or ketones having the formulas: $R_{16}CHO$, $R_{16\ CH2}CHO$, $R_{17}(C=O)R_{18}$ and $R_{17}CH_2(C=O)R_{18}$, where $R_{16}$, $R_{17}$, and $R_{18}$ can be the same or different and are each independently a straight or branched chain hydrocarbyl or aryl group that contains from 1 to 18 carbon atoms, preferably from 1 to 8 carbon atoms. Typically a solvent such as isobutanol is employed in the reaction. When $R_{16}$, $R_{17}$ and $R_{18}$ contain no α hydrogens, the reactions and reaction products of such aldehydes and ketones with the above described conventional deposit control additives containing primary amine functionality are:

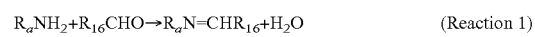  (Reaction 1)

  (Reaction 2)

where $R_a$ is an N-alkyl or N-polyamine moiety shown in Reactions 1 and 2 attached to a nitrogen atom in a primary amine functionality in any of the unmodified conventional deposit control additives described above-for example, in A of Formula I, in $R_4$ or $R_5$ in Formula II, or in B of Formula III—and within $R_a$ the alkyl group contains from 1 to 20 carbon atoms and the polyamine group contains from 2 to 12 nitrogen atoms and from 2 to 40 carbon atoms. When excess $R_aNH_2$ is employed, the product of Reaction 1 is $(R_a NH)_2 CHR_{16}$.

If the aldehyde or ketone does contain α-hydrogens, additional condensation products can be formed by aldol-like or Mannich-like reactions as in Reactions 3, 3', 4 and 4'.

(Reaction 3 - aldol-like)

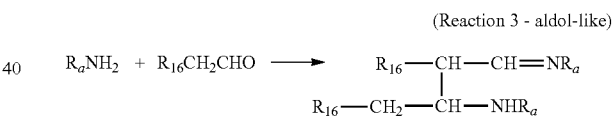

or (Reaction 3' - Mannich like)

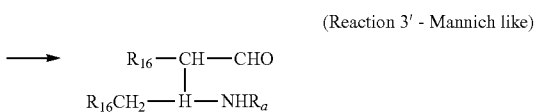

(Reaction 4 - Mannich like)

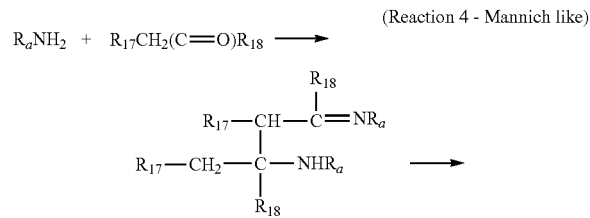

or (Reaction 4' - Mannich like)

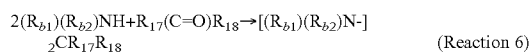

Generally an equimolar or slightly excess amount of carbonyl compound is used to limit the formation of multiple condensation products.

In addition a secondary amine functionality can react with $R_{16}CHO$ and $R_{17}(C=O)R_{18}$ according to:

$$2(R_{b1})(R_{b2})NH + R_{16}CHO \rightarrow [(R_{b1})(R_{b2})N\text{-}]_2 CHR_{16} \quad \text{(Reaction 5)}$$

$$2(R_{b1})(R_{b2})NH + R_{17}(C=O)R_{18} \rightarrow [(R_{b1})(R_{b2})N\text{-}]_2 CR_{17}R_{18} \quad \text{(Reaction 6)}$$

where $R_{b1}$ and $R_{b2}$ are independently each an N,N-dialkyl or N-polyamine shown in Reactions 5 and 6 attached to a nitrogen atom in the aforesaid secondary amine functionality, and each alkyl group therein contains from 1 to 20 carbon atoms and each polyamine group therein contains 2 to 12 nitrogen atoms and 2 to 40 carbon atoms, and $R_{16}$, $R_{17}$ and $R_{18}$ have no α-hydrogens.

However, if the aldehyde or ketone does contain α-hydrogens, a typical product will be the enamine:

$$(R_{b1})(R_{b2})NH + R_{16}CH_2CHO \rightarrow (R_{b1})(R_{b2})NCH=CHR_{16} \quad \text{(Reaction 7)}$$

$$(R_{b1})(R_{b2})NH + R_{17}CH_2(C=O)R_{18} \rightarrow (R_{b1})(R_{b2})NCR_{17}=CHR_{18} \quad \text{(Reaction 8)}$$

As in the case of the primary amines, Mannich-like products can be formed from a secondary amine functionality, as follows:

$$(R_{b1})(R_{b2})NH + R_{16}CH_2CHO \rightarrow (R_{b1})(R_{b2})NCH(CHR_{16}CHO)CH_2R_{16} \quad \text{(Reaction 9)}$$

$$(R_{b1})(R_{b2})NH + R_{17}CH_2(C=O)R_{18} \rightarrow (R_{b1})(R_{b2})NR_{18}(CHR_{17}(C=O)R_{18})CH_2R_{17} \quad \text{(Reaction 10)}$$

When the aldehyde or ketone is an α,β-unsaturated carbonyl compound, such as mesityl oxide (4-methyl-3-penten-2-one), the following reaction can occur by Michael-type addition:

$$R_aNH_2 + \text{mesityl oxide} \rightarrow R_aNHC(CH_3)_2CH_2(C=O)CH_3 + R_aNHC(CH_3)_2CH_2(C=NR_a)CH_3 + (CH_3)_2C=C\text{-}(C=NR_a)CH_3 \quad \text{(Reaction 11)}$$

$$(R_{b1})(Rb_2)NH + \text{mesityl oxide} \rightarrow (R_{b1})(R_{b2})NC(CH_3)_2CH_2(C=O)CH_3 \quad \text{(Reaction 12)}$$

The resulting carbonyl amine compounds could react further with the amine functionality, but an equimolar or slight excess amount of carbonyl can be used to prevent this further reaction.

When the amine is a polyethylene polyamine, for example, ethylene diamine, diethylene triamine, triethylene tetramine, and the like, the following reactions produce compositions that have cyclic structures:

(Reaction 13)

$$R_aNHCH_2CH_2NH_2 + R_{16}CHO \longrightarrow$$

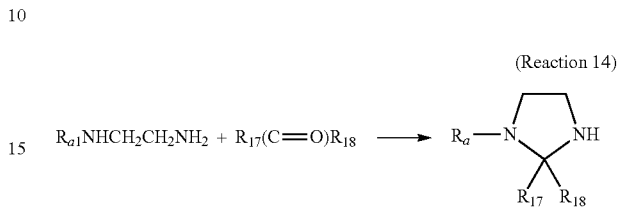

(Reaction 14)

$$R_{a1}NHCH_2CH_2NH_2 + R_{17}(C=O)R_{18} \longrightarrow$$

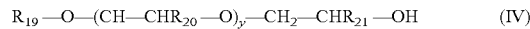

The deposit control additive of the present invention is employed in the aforesaid liquid automotive fuel at a level in the range of from about 50 preferably from about 100, to about 4000, preferably to about 2000, more preferably to about 1000 parts per million by volume.

An additional material that may optionally be used with the gasoline detergent additive composition of the present invention is a fluidizer or solvent, for example, an alkoxy mono- or poly(oxylene) alcohol and/or an aliphatic or aromatic organic solvent. The alkoxy mono- or poly (oxyalkylene) alcohol which may be employed as a fluidizer or solvents in the present invention has the following general formula:

$$R_{19}\text{—O—(CH—CHR}_{20}\text{—O)}_y\text{—CH}_2\text{—CHR}_{21}\text{—OH} \quad \text{(IV)}$$

wherein $R_{19}$ is an alkyl group of 1 to about 10 carbon atoms, and $R_{20}$ and $R_{21}$ are independently hydrogen or methyl, and y is an integer from 0 to 4. $R_{19}$ is preferably an alkyl group of 2 to 6 carbon atoms, $R_{20}$ and $R_{21}$ are preferably hydrogen, and y is preferably an integer from 0 to 2. More preferably, $R_{19}$ is an alkyl group of 4 carbon atoms (i.e., butyl), $R_{20}$ and $R_{21}$ are hydrogen, and y is 0.

Suitable alkoxy mono- or poly(oxyalkylene) alcohols for use in the present invention include, for example, 2-methoxyethanol, 2-ethoxyethanol, 2-n-butoxyethanol, 1-methoxy-2-propanol, 1-ethoxy-2-propanol, 1-n-butoxy-2-propanol, diethylene glycol methyl ether, diethylene glycol butyl ether, propylene ethylene glycol methyl ether, propylene ethylene glycol butyl ether, dipropylene glycol methyl ether, dipropylene glycol butyl ether, and the like, including mixtures thereof. A preferred alkoxy mono-or poly (oxyalkylene) alcohol is 2-n-butoxyethanol. A commercial 2-n-butoxyethanol, or ethylene glycol mono-butyl ether, is available as EB Butyl Cellusolve from Union Carbide, a subsidiary of Dow Chemical Company.

An aliphatic or aromatic hydrocarbyl organic solvent or fluidizer may also be employed in the present invention. Suitable aromatic solvents include benzene, toluene, xylene or higher boiling aromatics or aromatic thinners, such as a $C_9$ aromatic solvent. Suitable aliphatic solvents include dearomatized solvents such as Exxsol D40 and D60, available from ExxonMobil, other aliphatic solvents, such as D15-20 Naphta, D115-145 Naphtha and D31-35 Naphtha, also available from ExxonMobil, and nonaromatic mineral spirits, and the like. A preferred solvent or fluidizer for use in the present invention is a $C_9$ aromatic solvent.

Preferably, the solvent employed will be a mixture of both an alkoxy mono- or poly(oxyalkylene) alcohol and an aliphatic or aromatic organic solvent. In a particularly preferred embodiment, the solvent will be a mixture of 2-n-butoxyethanol and a C9 aromatic solvent.

Further conventional components and assistants that may also be employed are corrosion inhibitors, for example based on ammonium salts of organic carboxylic acids, which salts tend to form films, or on heterocyclic aromatics in the case of corrosion protection of nonferrous metals, antioxidants or stabilizers, for example based on amines, such as p-phenylenediamine, dicyclohexylamine or derivatives thereof and on phenols, such as 2,4-di-tert-butylphenol or 3,5-di-tert-butyl-4-hydroxyphenylpropionic acid, dehazers, demulsifiers, antistatic agents, metallocenes such as ferrocene or methylcyclopentadienyl manganese tricarbonyl, lubricity additives (different from compound (I)), such as certain fatty acids, alkenylsuccinic esters, bis(hydroxyalkyl)fatty amines, hydroxyacetamides and castor oil, antiknock additives, anti-icing additives, octane requirement additives, and also colorants (markers). Sometimes amines are also added to adjust the pH of the fuel.

The present invention will be explained in more detail below by reference to the following examples. However, the present invention should not be construed as being limited thereto.

GENERAL METHODS FOR EXAMPLES

Where provided, intake valve deposit(s) (IVD) were measured by weighing the dirty valve and subtracting the weight of clean valve as measured before the testing began, consistent with ASTM D6201-97, "Standard Test Method for Dynamometer Evaluation of Unleaded Spark-Ignition Engine Fuel for Intake Valve Deposit Formation". Coordinating Research Council (CRC) ratings, where given, were designated according to the "CRC Manual No. 16 Carburetor and Induction System Rating Manual" for visually rating the condition of intake valves (10=clean, 1=very heavy deposits).

EXAMPLE 1

A modified deposit control additive of the present invention, iso-BuPIBA #1, was prepared by refluxing 3.64 grams of isobutyraldehyde with 176 grams of AP-NA4M and 20 grams of isobutanol as a solvent for 3 hours. AP-NA4M is a formulated PIB amine type conventional deposit control additive manufactured by BASF Corporation including fluidizer, demulsifier and corrosion inhibitor and contains approximately 0.26 milli-equivalents of nitrogen. The equivalents of isobutyraldehyde added were 1.1 times the equivalents of nitrogen in the AP-NA4M. Infrared spectroscopy indicated conversion of about 79% of the aldehyde carbonyl and the appearance of an imine absorption.

All of the resulting iso-BuPIBA #1 was mixed with 83.5 gallons of all hydrocarbon conventional regular gasoline and 16.5 gallons of isobutanol. The resulting fuel blend would have contained four times the LAC dose of the conventional deposit control additive if the conventional deposit control additive had not been modified. This fuel blend is designated "Gas-BuOH #1".

A reference fuel designated "Gas-BuOH #2" was prepared by mixing 83.5 gallons of all hydrocarbon conventional regular gasoline and 16.5 gallons of iso-butanol and 176 grams of AP-NA4M. This fuel blend contained four times the LAC dose of the conventional deposit control additive.

A second reference fuel, designated "Gas-BuOH #3", was prepared by mixing 83.5 gallons of all hydrocarbon conventional regular gasoline and 16.5 gallons of isobutanol. This fuel blend contained no deposit control additive.

A third reference fuel, designated "Gas base" was 100 gallons of the all hydrocarbon conventional regular gasoline. This fuel blend contained no isobutanol and no deposit control additive.

Each of the above four fuels was evaluated for intake-valve deposit keep-clean performance by running them for 40 hours on a General Motors 3.8 liter V-6 engine and dynamometer test bed. The engine ran a repeated cycle consisting of two modes: 2600 rpm at 56 ft-lbs torque for 190 seconds followed by 2900 rpm at 99 ft-lbs torque for 25 seconds. Speed/load changes were accomplished with approximately a 30 second ramp up or ramp down as needed to maintain engine-dynamometer control.

Results of these experiments are shown in Table 1. The Gas-base fuel was formulated to give a relatively high deposit level. So the high deposit level and low CRC rating shown in Table 1 was expected. When isobutanol was added to the Gas-BuOH#3 fuel, there was no significant change in the deposit or rating. When a conventional deposit control additive was added to the isobutanol-gasoline blend Gas BuOH#2, a marked reduction of deposit was observed. When iso-BUPIBA#1, a deposit control additive of the present invention was used, an IVD reduction and improved CRC rating similar to that obtained when a conventional deposit control additive was observed. These experiments show that a deposit control additive of the present invention has at least similar efficacy as a conventional deposit control additive.

TABLE 1

| Fuel | Iso-butanol, % | Deposit Control Additive | CRC rating | IVD Average, mg/valve |
|---|---|---|---|---|
| Gas-base | None | None | 8.3 | 256.2 |
| Gas-BuOH #3 | 16.5 | None | 8.6 | 213.2 |
| Gas-BuOH #2 | 16.5 | AP-NA4M | 9.5 | 28.8 |
| Gas-BuOH #1 | 16.5 | iso-BuPIBA #1 | 9.5 | 25.7 |

A similar preparation of the deposit control additive of the present invention was made for use in fuel blends evaluated by a low-temperature valve-sticking test. A mixture of 2.00 grams of iso-butyraldehyde, 96.8 grams of AP-NA4M and 20 grams of isobutanol as solvent was refluxed to make iso-BuPIBA#2, a deposit control additive of the present invention. Infrared spectroscopy indicated conversion of about 58% of the aldehyde carbonyl and appearance of an imine absorption. All of the resulting iso-BuPIBA#2 was mixed with 45.92 gallons of a winter grade all hydrocarbon regular gasoline and 9.08 gallons of isobutanol to make the test fuel designated Wgas-BuOH #4. This fuel blend would have contained four times the LAC dose of the conventional deposit control additive if the conventional deposit control additive had not been modified.

A reference fuel designated "Wgas-BuOH #5" was prepared by mixing 45.92 gallons of winter grade all hydrocarbon regular gasoline and 9.08 gallons of iso-butanol and 60.5 grams of AP-NA4M. This fuel blend contained four times the LAC dose of the conventional deposit control additive.

A second reference fuel, designated "Wgas-BuOH #6", was prepared by mixing 45.92 gallons of winter grade all hydrocarbon regular gasoline and 9.08 gallons of iso-butanol and 60.5 grams of AP-NA4M. This fuel blend contained 2.5 times the LAC dose of the conventional deposit control additive.

A third reference fuel designated "Wgas-BuOH base" was prepared by mixing 45.92 gallons of winter grade all hydrocarbon regular gasoline and 9.08 gallons of iso-butanol. This fuel blend contained no deposit control additive.

All four of the above fuels were tested at Southwest Research Institute according to its standard Chevrolet Truck Valve Sticking Test. Briefly, that test was performed by driving the truck having a 5.0 liter V-8 engine with the test fuel over four cycles consisting of 56 minutes at 55 mph and 3 minute at idle, with a 1 minute ramp up or ramp down between idle and speed. After the driving cycles were completed, the test vehicle was cold soaked for 16 hours at −20° C. Following the cold soak, a cold engine compression test was performed to determine if valve sticking had occurred. This entire test sequence was repeated on two more days for a total of 3 sequences. If all valves stuck on all days a maximum total of 24 valves could stick.

Low temperature valve sticking test results are shown in Table 2. The iso-butanol fuel itself passed the test, but the conventional deposit control additive did not pass at either high (4X LAC) or lower (2.5X LAC) treat rates. The deposit control additive of the present invention did pass the test even though it was used in an amount that was equivalent to a high treat rate equivalent to 4X of conventional deposit control additive.

TABLE 2

| Fuel | Iso-butanol, % | Deposit Control Additive, treat rate (LAC) | Total stuck valves | Test Result |
|---|---|---|---|---|
| Wgas-BuOHbase | 16.5 | None | 0 | Pass |
| Wgas-BuOH #6 | 16.5 | AP-NA4M, 2.5X | 2 | Fail |
| Wgas-BuOH #5 | 16.5 | AP-NA4M, 4X | 3 | Fail |
| Wgas-BuOH #4 | 16.5 | iso-BuPIBA #2 | 0 | Pass |

EXAMPLE 2

A sequence similar to Example 1 was employed with a polyether amine type of deposit control additive. A deposit control additive of the present invention, iso-BuPEA #1, was prepared by refluxing 6.00 grams of isobutyraldehyde with 228 grams of HiTec® 6400 and 20 grams of isobutanol as solvent for 3 hours. HiTec 6400 is a formulated polyether amine (PEA) type of conventional deposit control additive manufactured by Afton Chemical Company and contains approximately 0.25 milli-equivalents of nitrogen. The equivalents of isobutyraldehyde added were 1.5 times the equivalents of nitrogen in HiTec 6400. Infrared spectroscopy indicated conversion of about 85% of the aldehyde carbonyl and appearance of an imine absorption.

All of the resulting iso-BuPEA #1 was mixed with 83.5 gallons of conventional all hydrocarbon regular gasoline and 16.5 gallons of isobutanol. This fuel blend would have contained four times the LAC dose of the conventional deposit control additive if the the conventional deposit control additive had not been modified. This fuel blend is designated "Gas-BuOH #4".

A reference fuel designated "Gas-BuOH #5" was prepared by mixing 83.5 gallons of conventional all hydrocarbon regular gasoline and 16.5 gallons of iso-butanol and 228 grams of HiTec® 6400. This fuel blend contained four times the LAC dose of the conventional deposit control additive.

Each of the above two fuels was evaluated for intake-valve deposit keep clean performance by running them for 40 hours on a General Motors 3.8 liter V-6 engine and dynamometer test bed as described in Example 1. The results and comparison to other reference fuels described in Example 1 are shown in Table 3. When the the conventional deposit control additive was added to the isobutanol-gasoline blend, Gas-BuOH#5, a marked reduction of deposit is observed,. When the PEA deposit control additive of the present invention of the present invention, iso-BUPEA#1, was used, an IVD reduction and improved CRC rating similar to the conventional deposit control additive was observed. These experiments demonstrate that the PEA deposit control additive of the present invention has similarly efficacy as the conventional deposit control additive.

TABLE 3

| Fuel | Iso-butanol, % | Deposit Control Additive | CRC rating | IVD Average, mg/valve |
|---|---|---|---|---|
| Gas-base | None | None | 8.3 | 256.2 |
| Gas-BuOH #3 | 16.5 | None | 8.6 | 213.2 |
| Gas-BuOH #5 | 16.5 | HiTec ® 6400 | 9.5 | 28.0 |
| Gas-BuOH #4 | 16.5 | iso-BuPEA #1 | 9.3 | 30.2 |

A similar preparation of the PEA deposit control additive of the present invention was made for use in fuel blends evaluated by a low-temperature valve-sticking test. A mixture of 3.68 grams of iso-butyraldehyde, 118.1 grams HiTec® 6400 and 20 grams of isobutanol as solvent was refluxed to make a PEA deposit control additive of the present invention designated iso-BuPEA#2. Infrared spectroscopy indicated conversion of about 93% of the aldehyde carbonyl and appearance of an imine absorption. All of the resulting iso-BuPEA#2 was mixed with 45.92 gallons of a winter grade all hydrocarbon regular gasoline and 9.08 gallons of isobutanol to make test fuel Wgas-BuOH #7. This fuel blend would have contained six times the LAC dose of the conventional deposit control additive if the conventional deposit control additive had not been modified.

A reference fuel, designated "Wgas-BuOH #8", was prepared by mixing 45.92 gallons of winter grade all hydrocarbon regular gasoline and 9.08 gallons of iso-butanol and 250.8 grams of HiTec® 6400. This fuel blend contained eight times the LAC dose of the conventional deposit control additive.

A second reference fuel designated "Wgas-BuOH #9" was prepared by mixing 45.92 gallons of winter grade all hydrocarbon regular gasoline and 9.08 gallons of iso-butanol and 125.4 grams of HiTec® 6400. This fuel blend contained four times the LAC dose of the conventional deposit control additive.

A third reference fuel designated "Wgas-BuOH #10" was prepared by mixing 48.68 gallons of winter grade all hydrocarbon regular gasoline and 6.32 gallons of iso-butanol and 188.1 grams of HiTec® 6400. This fuel blend contained six times the LAC dose of the conventional deposit control additive but a lower isobutanol concentration.

All four of the above fuels were tested at Southwest Research Institute according to its standard Chevrolet Truck Valve Sticking Test as described in Example 1. Low temperature valve sticking test results are shown in Table 4. The fuels with the conventional deposit control additive did not pass the test at either high (8X LAC) or low (4X LAC) treat rates. However, the fuel with the deposit control additive of the present invention passed at the equivalent of 6X LAC. An additional test using fuel with conventional deposit control additive but a lower iso-butanol concentration (11.5%) passed the test indicating significant test dependency on the base fuel solvency characteristics for the deposit control additive.

TABLE 4

| Fuel | Iso-butanol, % | Deposit Control Additive, treat rate (LAC) | Total stuck valves | Test Result |
|---|---|---|---|---|
| Wgas-BuOH #8 | 16.5 | HiTec ® 6400, 8X | 2 | Fail |
| Wgas-BuOH #9 | 16.5 | HiTec ® 6400, 4X | 2 | Fail |
| Wgas-BuOH #10 | 11.5 | HiTec ® 6400, 6X | 0 | Pass |
| Wgas-BuOH #7 | 16.5 | iso-BuPEA #2 | 0 | Pass |

EXAMPLE 3

Four deposit control additives of the present invention were prepared using the amounts in Table 5 by refluxing for 3 hours. The molar ratio of amine to carbonyl compound was 1:1 for all these additives. These four additives and/or AP-NA4M were combined with an all hydrocarbon regular gasoline base mixed with n-butanol in a 9:1 volume:volume ratio to make fuels described in Table 6.

TABLE 5

| Carbonyl compound | Carbonyl compound, weight, grams | AP-NA4M weight, grams | n-Butanol weight, grams | Modified DCA designation |
|---|---|---|---|---|
| 4-methyl-3-pente-2-one | 0.70 | 27.5 | 20.8 | ModPIBA #1 |
| 4-methyl-3-pente-2-one | 2.25 | 88.0 | 20.0 | ModPIBA #2 |
| n-butyraldehyde | 1.65 | 88.0 | 20.0 | ModPIBA #3 |
| Acetone | 1.33 | 88.0 | 20.0 | ModPIBA #4 |

The fuels in Table 6 were tested for IVD keep clean performance by running them in a General Motors 3.8 liter V-6 engine dynamometer test rig for 20 hours. The continuously repeated speed-load cycle for these tests consisted of 2000 rpm at manifold absolute pressure of 230 kPa (approximately 9 ft-lb) for 240 seconds and 2800 rpm at manifold absolute pressure of 540 kPa (approximately 60 ft-lbs) for 480 seconds with an approximately 30 second ramp up or ramp down transition between conditions.

TABLE 6

| Fuel | DCA | DCA equivalent treat rate, LAC | CRC Valve Rating | Average IVD, mg |
|---|---|---|---|---|
| Baseline 2.5X | AP-NA4M | 2.5X | 8.9 | 47.3 |
| unmodified + modified #1 | AP-NA4M + ModPIBA #1 | 1.25X + 1.25X | 9.0 | 49.0 |
| Baseline 4.0X | AP-NA4M | 4.0X | 9.2 | 31.3 |
| Modified #1 | ModPIBA #2 | 4.0X | 9.1 | 29.7 |
| Modified #2 | ModPIBA #3 | 4.0X | 8.8 | 46.8 |
| Modified #3 | ModPIBA #4 | 4.0X | 9.2 | 30.8 |

The results in Table 6 demonstrate that the deposit control additives of the present invention perform similarly to the conventional deposit control additives Thus, the performance in internal combustion engines of the detergent or deposit control additives of the present invention is not affected by carbonyl impurities that may be present in bio-derived fuels or blends and have improved capability. The additives of the present invention exhibit intake-valve keep-clean and clean-up performance that is comparable to the aforesaid conventional additives described above. Moreover, the low temperature valve-sticking performance of the additives of the present invention is improved such that the deposit control additives of this invention pass a low-temperature valve-sticking test at concentration levels at which the aforesaid unmodified additives do not pass.

From the above description, it is apparent that the objects of the present invention have been achieved. While only certain embodiments have been set forth, alternative embodiments and various modifications will be apparent from the above description to those skilled in the art and are within the spirit and scope of the present invention.

That which is claimed is:

1. A liquid automotive fuel comprising from about 70 to about 95 volume percent of hydrocarbons boiling in the gasoline range, from about 5 to about 30 volume percent of at least one alcohol, and an imine or tertiary amine product of the reaction between
   (a) at least one aldehyde having the formula $R_{16}$ CHO or $R_{16}$ $CH_2$ CHO, wherein $R_{16}$ is a straight or branched chain hydrocarbyl or aryl group that contains from 1 to 18 carbon atoms, and
   (b) a primary or secondary amine functionality of the formula:

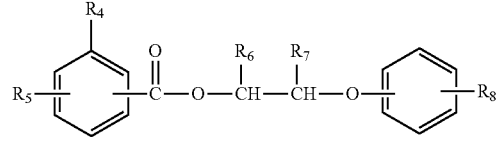

wherein: $R_4$ is nitro or $-(CH_2)_n-NR_9R_{10}$, wherein $R_9$ and $R_{10}$ are independently hydrogen or lower alkyl having 1 to 6 carbon atoms and n is 0 or 1; $R_5$ is hydrogen, hydroxy, nitro or $-NR_{11}R_{12}$, wherein $R_{11}$ and $R_{12}$ are independently hydrogen or lower alkyl having 1 to 6 carbon atoms; $R_6$ and $R_7$, are independently hydrogen or lower alkyl having 1 to 6 carbon atoms; and $R_8$ is a polyalkyl group having an average molecular weight in the range of about 450 to 5,000.

2. The liquid automotive fuel of claim 1 wherein $R_{16}$ of the aldehyde contains from 1 to 8 carbon atoms.

3. The liquid automotive fuel of claim 1 wherein $R_{16}$ contains from 1 to 12 atoms.

4. The liquid automotive fuel claim 1 wherein the liquid automotive fuel comprises about 2 to about 30 volume percent of the at least one alcohol.

5. The liquid automotive fuel of claim 1 wherein the at least one alcohol comprises ethanol or a butanol or both.

6. The liquid automotive fuel of claim 5 wherein the at least one alcohol comprises a butanol isomer.

7. The liquid automotive fuel of claim 6 wherein the at least one alcohol comprises isobutanol.

8. The liquid automotive fuel of claim 1 comprising the imine or tertiary amine product of the reaction between the aldehyde and a primary amine functionality.

9. The liquid automotive fuel of claim 1 comprising from about 50 to about 4000 parts per million by volume of the imine or tertiary amine.

10. The liquid automotive fuel of claim 9 wherein the imine or tertiary amine is at a level of from about 100 to about 2000 parts per million by volume.

11. The liquid automotive fuel of claim 10 wherein the imine or tertiary amine is at a level of from about 100 to about 1000 parts per million by volume.

* * * * *